United States Patent [19]

Bonazza et al.

[11] 4,247,300

[45] Jan. 27, 1981

[54] IMIDAZOLINE FUEL DETERGENTS

[75] Inventors: Benedict R. Bonazza, Bartlesville, Okla.; Hans D. Holtz, deceased, late of Bartlesville, Okla., by Marilyn T. Holtz, executrix

[73] Assignee: Phillips Petroleum Company, Bartlesville, Okla.

[21] Appl. No.: 900,552

[22] Filed: Apr. 27, 1978

[51] Int. Cl.³ .......................... C10L 1/14; C10L 1/22
[52] U.S. Cl. ............................................ 44/63; 44/72
[58] Field of Search ...................... 44/72, 63; 548/352; 252/33

[56] References Cited

U.S. PATENT DOCUMENTS

| Re. 23,227 | 5/1950 | Blair et al. | 548/352 |
| 2,214,152 | 9/1940 | Wilkes | 548/352 |
| 2,622,018 | 12/1952 | White et al. | 44/72 |
| 2,622,067 | 12/1952 | White et al. | 548/352 |

FOREIGN PATENT DOCUMENTS 1181985  11/1964  Fed. Rep. of Germany ........... 548/352

*Primary Examiner*—Patrick Garvin
*Assistant Examiner*—Raymond K. Covington

[57] ABSTRACT

A detergent additive imidazoline prepared by reacting carboxylic acid with polyamine is combined into fuel for an internal combustion engine or lubricating oil as a composition suitable for reducing deposits in an internal combustion engine. In an embodiment of the invention, the imidazoline is further combined with a sulfonic acid to obtain a fuel detergent of improved operability.

4 Claims, No Drawings

IMIDAZOLINE FUEL DETERGENTS

BACKGROUND OF THE INVENTION

This invention relates to additives for hydrocarbons suitable for use in an internal combustion engine. In one of its aspects this invention relates to detergent additives for hydrocarbon fuels. In another of its aspects this invention relates to detergent additives for hydrocarbon lubricants. In still another of its aspects this invention relates to the reduction of deposits in an internal combustion engine.

If deposits are allowed to accumulate in an engine they can cause enrichment of the fuel to air ratio which would result in increased hydrocarbon and carbon monoxide emissions, reduced fuel economy, and driving problems such as rough idling and frequent stalling. Among the most important considerations of the effects of engine deposits are those having a bearing on the environment. With the advent of pollution standards for automobile exhaust it has become important that fuel additives not contain phosphorus or metal ions which tend to poison the catalysts in automotive engine exhaust converter systems. It is, therefore, of interest to discover new compounds or compositions, which contain no phosphorus or metals, that are useful as detergent additives for fuels and lubricants.

It is therefore an object of this invention to provide compounds that are useful as detergent additives for internal combustion engine fuels and lubricants. It is another object of this invention to provide a method for producing detergent additives. It is still another object of this invention to provide an ashless detergent fuel composition combining an ashless fuel detergent additive with a hydrocarbon suitable for use as fuel in an internal combustion engine. It is still another object of this invention to provide a method for reducing deposits in internal combustion engines.

Other aspects, objects, and the various advantages of this invention will become apparent upon reading the specification and the appended claims.

STATEMENT OF THE INVENTION

According to this invention, a detergent composition is provided in which a fuel for an internal combustion engine or a lubricating oil is combined with an imidazoline. In an embodiment of the invention, the imidazoline is reacted with a sulfonic acid.

Detergent additives of this invention are made by reaction of a polyamine with a carboxylic acid to produce an imidazoline. In the carboxylic acid, RCOOH, R is a hydrocarbyl radical of about 7-99 carbon atoms, preferably about 11-25 carbon atoms. These hydrocarbyl radicals include alkyl, alkenyl, cycloalkyl, cycloalkenyl, aryl and combinations such as alkaryl, aralkyl, alkylcycloalkyl, arylcycloalkyl, aralkenyl, and arylcycloalkenyl. Suitable examples are capric acid, myristic acid, stearic acid, oleic acid; and also any isomers or mixtures of isomers of isostearic acid, phenylstearic acid, naphthyl lauric acid, phenylcyclohexylcarboxylic acid, cyclohexylbenzoic acid, and the like.

Polyamines required to make imidazolines have the general formula $H_2NCH_2CH_2NH(CH_2CH_2NR')_aH$ where R' can be hydrogen, alkyl or $(CH_2CH_2NH)_bH$. The sum of a and b should not exceed 10; a can have values between 0 and 10; b can range between zero and 8. Suitable examples of polyamines include ethylenediamine, diethylenetriamine, tetraethylenepentamine, hexaethyleneheptamine, and polyamines such as these in which internal (secondary) nitrogens bear the $(CH_2CH_2NH)_bH$ group.

The reaction by which imidazolines are made involves two consecutive nitrogen atoms in the amine including a terminal (primary) nitrogen. There must be at least one pair of nitrogen atoms in the polyamine in which a primary nitrogen is adjacent to a secondary (or another primary) nitrogen. Potentially one imidazoline ring is formed for each such combination in the polyamine. The reaction by which imidazolines are made is preceded by reaction between the carboxylic acid and amine nitrogen with the elimination of a mole of water to make an amide. Subsequent reaction with the second nitrogen, which effects ring closure, involves elimination of a second mole of water. Determination of the quantity of water evolved from the reactants provides the criterion to determine how far reaction has proceeded.

The reaction of the carboxylic acid and the polyamine form an imidazoline as set forth in the reaction equation below:

$RCOOH + H_2NCH_2CH_2NH(CH_2CH_2NR')_aH \longrightarrow$

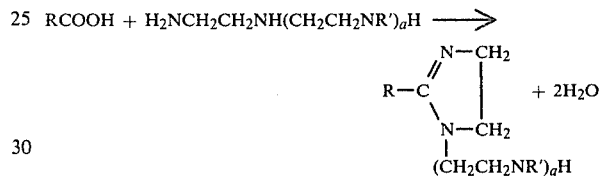

$+ 2H_2O$

In the imidazoline product above, R, R', and a are as defined for the carboxylic acid and polyamine above.

The reaction is carried out under conditions in which water is removed promptly. Solvents such as liquid hydrocarbons can provide the reaction medium, or the reactants can be combined neat. Suitable hydrocarbon solvents for the reaction are preferably aromatics, but they can be paraffinic or naphthenic. Desirably their boiling range is from about 100° to about 300° C. so the reaction can be conducted under reflux conditions. The temperature for formation of imidazolines lies in the range of about 100° to about 300° C. As mentioned, evolved water is removed from the reactor promptly to permit reaction to go to completion. When solvent is used this may be done by condensing the refluxing solvent and discarding the water phase. When no solvent is used, evolved water vapor is swept from the reactor; an inert gas such as nitrogen is suitable for purging the reactor. Although it is not required, use of an inert, oxygen-free, gas blanket is recommended during the imidazoline synthesis to prevent possible undesirable oxidation reactions. Extent of reaction can be followed by measuring the quantity of water that has been liberated. The additive of this invention requires the production of more than 1.5 moles of water per mole of reacted carboxylic acid; this assures that the concentration of imidazoline is larger than the amide concentration in the reaction product.

When desired, and to improve its water tolerance, the imidazoline additive is reacted with an arylsulfonic acid. A basic additive is preferred, so the amount of sulfonic acid used is not greater than the stoichiometric quantity necessary completely to neutralize the amine nitrogen. Suitable sulfonic acids have the general formula $R''SO_3H$ where $R''$ is an aryl or an alkaryl group with 6 to about 100 carbon atoms. Benzenesulfonic acid, isopropylbenzenesulfonic acid, cyclohexylbenzenesulfonic acid, dodecylbenzenesulfonic acid, and dioctylbenzenesulfonic acid are suitable examples. The ratio of sulfonic acid to imidazoline required to prepare the finished additive may be determined by titrating them separately with standard base and standard acid, respectively, using a glass electrode pH meter. Samples are dissolved in titration solvent (equal volumes of benzene and isopropanol plus 0.5 vol. percent water) for the titration. The quantity of sulfonic acid added to the imidazoline is chosen to make a product having pH of about 7–9. The reaction of sulfonic acid and imidazoline is effected by warming the mixture to about 50°–75° C. for 15 to 30 minutes with stirring adequate to produce a homogeneous phase. Viscous reactants are conveniently thinned by dilution with lubrication stock hydrocarbons or other common hydrocarbon solvents before this neutralization reaction.

The imidazolines, or the products of their reaction with sulfonic acid, are detergent additives which can be added to motor fuel in the concentration range about 1–100 lbs/1000 barrels (0.00285–0.285 gm/liter), preferably about 5–30 lbs/1000 barrels, to prevent harmful carburetor and fuel intake system deposits.

These additives are also useful when added to lubricating stock. They serve as detergents to help keep the engine parts clean. Other additives, such as viscosity index improvers, antioxidants, and the like can be used in formulation with the additives of this invention.

The following examples will help to illustrate this invention.

EXAMPLE I

Reaction of isostearic acid and tetraethylenepentamine: To a 500 ml round bottom flask fitted with a Barrett water trap with associated water-cooled condenser, and with a thermowell containing a thermometer were added 79.5 gm (0.28 mole) isostearic acid, 26.5 gm (0.14 mole) tetraethylenepentamine, and about 50 cc of toluene. Reactants were blanketed with nitrogen that was admitted through a tube via the Barrett trap. The flask was heated to reflux (135° C.); in about 30 minutes 2.5 cc of water had been collected. Using a stopcock that permitted draining condensate from the Barrett trap, sufficient toluene was removed to raise the boiling point to about 170° C. In about three hours a total of 8.4 cc (0.47 mole) of water was collected. In 90 minutes of additional refluxing no more water was liberated. The amount of water collected represents complete reaction of the isostearic acid, equivalent to formation of about 70 percent imidazoline and 30 percent amide. By titration with standard HCl the equivalent weight of this additive was determined to be 568.

EXAMPLE II

Reaction with acid oil: To 15.3 gm (0.0269 equivalents) of the additive from Example I was added 34.7 gm (0.0270 equivalents) of acid oil made by sulfonating a 250 weight lubricating base stock with sulfur trioxide. The product of this neutralization, as a one percent solution in titration solvent (described above), had a pH of 8.6.

EXAMPLE III

Reaction with dodecylbenzene sulfonic acid: To 31.8 gm (0.0560 equivalents) of the additive from Example I was added 18.1 gm (0.0559 equivalents) of dodecylbenzene sulfonic acid—Witco Chemical's Sulframin 98 Hard Acid. The product of this neutralization, as a one percent solution in titration solvent, had a pH of 8.2.

EXAMPLE IV

Tests of additives: Additives whose preparation is described in the preceding examples were subjected to a series of tests in gasoline, at the concentrations listed.
1. Falcon engine test. 10 lbs/1000 barrels. (Additive from Example II at 20 lbs/1000 barrels because about half of the acid oil is unsulfonated paraffins and/or naphthenes).
2. Thin layer chromatography (TLC) test, for detergency. 7.63 wt. percent additive.
3. Spray gum deposit. 0.10 wt. percent additive.
4. Water tolerance test. Twice the concentration used in Falcon engine test.

The Falcon engine test, briefly, involves use of the test gasoline in a 170 cubic inch displacement 6-cylinder automobile engine with a removable carburetor throat insert. The engine operated for 23 hours at 1800 rpm and 11.4 brake horsepower. After conclusion of the test, the removable insert was weighed to give the weight of deposits. Results are compared with tests using a base gasoline which was commercial leaded gasoline.

The TLC test for detergency provides a basis for evaluating potential carburetor detergents in a much shorter period of time than the Falcon engine test requires. It involves use of a toluene solution of the additive being tested to move a small specimen of carburetor deposit in a developing paper chromatogram. Results are reported as follows:

| Numerically | Verbally | Description |
|---|---|---|
| 4 | Poor | Deposit remains with no or very little movement. |
| 6 | Fair | About half of deposit is removed and carried upwards: possible streaking full length of solvent movement. |
| 8 | Good | much of deposit moves with solvent front or close to it: only a small part of it remains at origin. |
| 9 | Good-excellent | Deposit is completely moved, and essentially moves with solvent front. |

This test was developed to screen additives without using the time that engine tests require. Additives that fail this test always fail the engine test, but those that pass it should be confirmed by engine test data. A rating of 4 is considered to be a failure.

The spray gump deposit test provides a measure of the thermal stability of the additive being evaluated. The test is carried out by spraying 250 cc of gasoline containing the additive and 0.04 wt. percent Santolube 395-X (a sulfurized terpene, to augment gum formation) into a tared aluminum pan maintained at 191° C. After spraying has ended the pan is cooled, washed in n-heptane, dried, and reweighed. Test results are reported as the gain in weight, in milligrams, per 250 cc gasoline.

The water tolerance test measures the propensity of the additive-gasoline solution to form undesirable aqueous emulsions. The test measures the amount of demulsifier which must be added to the additive-fuel blend to break the emulsions. The demulsifier used is Oronite OGA-473. Samples are tested by the ASTM standard test method "Water Reaction of Aviation Fuels" (ASTM D-1094-72) and the results are reported as the percent of demulsifier (based on the amount of additive present) required to give a 1 or 1b (pass) rating. Additives which require low percentages of demulsifier are considered to have superior water tolerance characteristics and those requiring more than 4 percent demulsifier fail the test.

Results of subjecting the additives from Examples I–III to these four tests are summarized:

| Additive | Falcon engine* | TLC | Spray gum | Water Tolerance |
|---|---|---|---|---|
| Example I | 80 | 9 | 0.1 mgm | Fail |
| Example II | 83 | 8 | 0.0 mgm | 2 |
| Example III | 80 | 9 | 0.0 mgm | 2 |

*Percent reduction in unwashed carburetor deposit relative to base fuel without additive.

Evaluation of the additives by the TLC screening procedure showed them to have good or good-excellent ratings for detergency; this was confirmed by the Falcon engine test in which all three additives reduced carburetor deposits by at least 80 percent. All additives gave excellent results in the spray gum test, leaving essentially no residue. The diisostearylimidazoline of tetraethylenepentamine (Example I) failed the water tolerance test. However, reaction with either acid oil or dodecylbenzenesulfonic acid produced an additive that readily passed the test.

We claim:

1. A composition comprising a hydrocarbon suitable as a fuel for an internal combustion engine and a detergent additive comprising the reaction product of an imidazoline of the formula

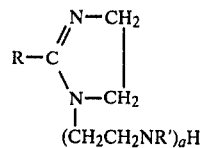

wherein R is a hydrocarbyl radical of 7–99 carbon atoms, R' is hydrogen, alkyl or $(CH_2CH_2NH)_bH$, a has a value of 0–10, and b has a value of 0–8 reacted with a sulfonic acid having the formula $R''SO_3H$ wherein R'' is chosen from among an aryl and an alkaryl group with 6–100 carbon atoms.

2. A method for reducing engine deposits in an internal combustion engine comprising the addition to the hydrocarbon fuel for the engine of a detergent fuel additive comprising the reaction product of an imidazoline of the formula

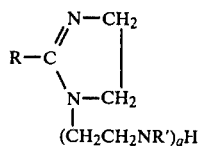

wherein R is a hydrocarbon radical of 7–99 carbon atoms, R' is hydrogen, alkyl or $(CH_2CH_2NH)_bH$, a has a value of 0–10, and b has a value of 0–8 reated with a sulfonic acid having the formula $R''SO_3H$ wherein R'' is chosen from among an aryl and an alkaryl group with 6–100 carbon atoms, said ashless fuel detergent being added in an amount effective to reduce engine deposits and using said hydrocarbon fuel with ashless fuel detergent additive as fuel in an internal combustion engine.

3. A method of claim 2 wherein said detergent fuel additive is present in the concentration range of about 1–100 lbs/1000 barrels of hydrocarbon fuel.

4. A composition of claim 1 in which said detergent additive is present in the concentration range of about 1–100 lbs/1000 barrels of hydrocarbon suitable as a fuel.

* * * * *